(12) United States Patent
Ohashi et al.

(10) Patent No.: US 7,074,903 B2
(45) Date of Patent: Jul. 11, 2006

(54) MONOCLONAL ANTIBODY SPECIFIC TO TARTRATE-RESISTANT ACID PHOSPHATASE 5B AND USE THEREOF

(75) Inventors: Tatsuya Ohashi, Koriyama (JP); Toshihide Miura, Koriyama (JP); Yoshihiko Igarashi, Mibumachi (JP); Kumiko Sasagawa, Koriyama (JP); Katsuhiro Katayama, Koriyama (JP)

(73) Assignee: Nitto Boseki Co., Ltd., Fukushima (JP)

( * ) Notice: Subject to any disclaimer, the term of this patent is extended or adjusted under 35 U.S.C. 154(b) by 0 days.

(21) Appl. No.: 10/424,726

(22) Filed: Apr. 29, 2003

(65) Prior Publication Data

US 2003/0204062 A1    Oct. 30, 2003

(30) Foreign Application Priority Data

Apr. 30, 2002   (JP)   ............................. 2002-128312

(51) Int. Cl.
    C07K 16/40    (2006.01)
    C12N 5/20     (2006.01)
    C12P 21/08    (2006.01)
    G01N 33/543   (2006.01)
    G01N 33/573   (2006.01)

(52) U.S. Cl. ............................. 530/388.26; 530/391.1; 435/7.4; 435/7.92; 435/7.94; 435/7.95; 435/21; 435/70.21; 435/40.52; 435/174; 435/177; 435/452; 435/338; 435/960; 435/975; 436/518; 436/528; 436/548

(58) Field of Classification Search ................. 435/7.1, 435/7.4, 7.92, 7.94, 7.95, 21, 40.5, 40.51, 435/40.52, 70.21, 452, 174, 177, 338, 960, 435/962, 975; 436/518, 528, 548, 811; 530/388.26, 530/391.1

See application file for complete search history.

(56) References Cited

U.S. PATENT DOCUMENTS 6,248,544 B1 *   6/2001   Halleen et al. .............. 435/7.4

FOREIGN PATENT DOCUMENTS

WO    WO 99/50662    10/1999

OTHER PUBLICATIONS

T. Onishi; "Study of Human Serum Tartrate-Resistant Acid Phosphatase"; *J. Nihon University Medical Association*; vol. 49, No. 9; 1990./English abstract on p. 911/Discussed in the specification.
K.-H. Lau et al.; "Characterization and Assay of Tartrate-Resistant Acid Phosphatase Activity in Serum: Potential Use to Assess Bone Resorption"; *Clinical Chemistry*; vol. 33, No. 4; pp. 458-462; 1987./Discussed in the specification.
A. Janckila et al.; "Tartrate-resistant Acid Phosphatase Isoform 5b as Serum Marker for Osteoclastic Activity"; *Clinical Chemistry*; vol. 47, No. 1; pp. 74-80; 2001.
M. Kraenzlin et al.; "Development of an Immunoassay for Human Serum Osteoclastic Tartrate-Resistant Acid Phosphatase"; *Journal of Clinical Endocrinology and Metabolism;* vol. 71, No. 2; pp. 442-451;1990./ Discussed in the specification.
J. Haleen et al.; "Two-Site Immunoassays for Osteoclastic Tartrate-Resistant Acid Phosphatase Based on Characterization of Six Monoclonal Antibodies"; *Journal of Bone and Mineral Research;* vol. 14., No. 3; pp. 464-469; 1999./ Discussed in the specification.
H. Bull et al.; "Reactivity and assay restriction profiles of monconal and polyclonal antibodies to acid phosphatases: a preliminary study"; *Immunology Letters;* vol. 70; pp. 143-149; 1999./Discussed in the specification.
S. Alatalo et al.; "Rapid Screening Method for Osteoclast Differentiation in Vitro That Measures Tartrate-resistant Acid Phosphatase 5b Activity Secreted into the Culture Medium"; *Clinical Chemistry;* vol. 46., No. 11; pp. 1751-1754; 2000./Discussed in the specification.
J. Halleen et al.; "Characterization of Serum Tartrate-Resistant Acid Phosphatase and Development of a Direct Two-Site Immunoassay"; *Journal of Bone and Mineral Research;* vol. 13, No. 4; pp. 683-687; 1998./Discussed in the specification.
Y. Nakasato et al.; "Clinical Significance of Immunoassays or Type-5 Tartrate-resistant Acid Phosphatase"; *Clinical Chemistry;* vol. 45; No. 12; pp. 2150-2157; 1999./Discussed in the specification.
K. Takahashi et al.; "Electrophoretic study of tartrate-resistant acid phosphatase isoforms in endstage renal disease and rheumatoid arthritis"; *Clinica Chimica Acta;* vol. 301; pp. 147-158; 2000./Discussed in the specification.
W. Lam et al.; "Biochemical Properties of Tartrate-Resistant Acid Phosphatase in Serum of Adults and Children"; *Clinical Chemistry;* vol. 24, No. 7; pp. 1105-1108; 1978.
W. Lam et al.; "Tartrate-Resistant (Band 5) Acid Phosphatase Activity Measured by Electrophoresis on Acrylamide Gel"; *Clinical Chemistry;* vol. 24., No. 2; pp. 309-312; 1978.
M. Nakanishi et al.; "Development of a Kinetic Assay for Band 5B Tartrate-resistant Acid Phosphatase Activity in Serum"; *Clinical Chemistry;* vol. 46; No. 4; pp. 469-473; 2000.

(Continued)

Primary Examiner—Long V. Le
Assistant Examiner—James L. Grun
(74) Attorney, Agent, or Firm—Westerman, Hattori, Daniels & Adrian LLP

(57) ABSTRACT

Monoclonal antibodies having a higher reactivity with tartrate-resistant acid phosphatase 5b (TRACP 5b) than tartrate-resistant acid phosphatase 5a (TRACP 5a) and having a higher specificity to TRACP 5b can be obtained by cell fusion using as antigens TRACP 5b purified from human osteoclasts. By using the monoclonal antibody, TRACP 5b in a sample can be detected specifically with a high sensitivity.

13 Claims, 3 Drawing Sheets

OTHER PUBLICATIONS

A. Hayman et al.; "Purple Acid Phosphatase of the Human Macrophage and Osteoclast"; *The Journal of Biological Chemistry;* vol. 269, No. 2; pp. 1294-1300; 1994.

A. Janckila et al.; "Characterization of Monoclonal Antiboides Specific to Human Tartrate-Resistant Acid Phosphatase"; *Hybridoma;* vol. 16, No. 2; pp. 175-182; 1997.

A. Janckila et al.; "Species Specificity of Monoclonal Antibodies to Human Tartrate-Resistant Acid Phosphatase"; *Biotechnic and Histochemistry;* vol. 73; No., 6; pp. 316-324; 1998.

M. Nakanishi et al.; "Improved method for measuring tartrate-resistant acid phosphatase activity in serum"; *Clinical Chemistry;* vol. 44, No. 2; pp. 221-225; 1998.

Copy of Communication and European Search Report dated Dec. 4, 2003.

J. Hallen et al., Journal of Bone and Mineral Research, "Tartrate-Resistant Acid Phosphatase 5b: A Novel Serum Marker of Bone Resorption", vol. 15, No. 7, Jul. 2000, pp. 1337-1345.

\* cited by examiner

1: PURIFIED TRACP5b
2: CM-Sepharose Pool
3: Molecular Marker

1: HUMAN SERUM
2: PURIFIED HUMAN TRACP 5b
3: PURIFIED HUMAN TRACP 5a

1: Molecular Marker
2: Fraction 26 (36.01KU/L)
3: Fraction 27 (44.80KU/L)
4: Fraction 28 (35.24KU/L)

1: Molecular Marker
2: PURIFIED HUMAN TRACP 5b
3: Baculoviral rhTRACP
4: PURIFIED HUMAN TRACP 5b Trk62

MONOCLONAL ANTIBODY SPECIFIC TO TARTRATE-RESISTANT ACID PHOSPHATASE 5B AND USE THEREOF

BACKGROUND OF THE INVENTION

1. Field of the Invention

The present invention relates to a monoclonal antibody specific to tartrate-resistant acid phosphatase 5b (TRACP 5b: otherwise known as osteoclast-derived tartrate-resistant acid phosphatase), hybridomas capable of producing the monoclonal antibody, a method of detecting TRACP 5b using the monoclonal antibody, and a kit for use in the detecting method.

The monoclonal antibody of the present invention enables one to specifically assay the activity of tartrate-resistant acid phosphatase 5b and is extremely useful as a marker for bone resorption in the field of medical treatments for bone diseases and clinical diagnosis.

2. Description of the Related Arts

It is reported that tartrate-resistant acid phosphatase (TRACP: Tartrate-Resistant Acid Phosphatase EC 3.1.3.2) in serum is an acid phosphatase derived largely from osteoclasts and that the assay of TRACP activity will be useful as a measure for evaluating the function of osteoclasts. Thus, keen attention was drawn to TRACP as a marker for bone resorption (KOTSU TAISHA MARKER (Bone Metabolism Marker), edited by Masao Fukunaga, Toshitaka Nakamura & Toshio Matsumoto, 1995, published by Medical Review, Inc.) Analysis of acid phosphatases in serum on polyacrylamide gel electrophoresis has identified 6 bands, which are bands 0 to 6 from the starting point. In these 6 bands, band 5 is resistant to tartrate treatment and therefore called band 5 tartrate-resistant acid phosphatase (TRACP 5). TRACP 5 is further separated into components located at bands 5a and 5b based on electrophoretic mobility, i.e., band 5a is abundant in sialic acid-binding carbohydrate chains and band 5b having less sialic acid-binding carbohydrate chains. The TRACP 5a enzyme originating from platelets, etc. does not change its blood level, but TRACP 5b changes the blood level accompanied by bone resorption. Therefore, TRACP 5b is considered to be the only acid phosphatase derived from osteoclasts that is resistant to inhibition by tartrate (JP2002-510050A).

Abbreviation of TRACP 5b to osteoclast-derived ACP is recommended also in Clin. Chem. 47:1497, 2001. Accordingly, throughout the specification, TRACP 5b is used to mean ACP derived from osteoclasts as a marker for bone resorption and osteoclast-derived tartrate-resistant acid phosphatase and tartrate-resistant acid phosphatase 5b are collectively referred to as TRACP 5b, unless otherwise indicated.

Conventional methods of assaying TRACP activity as a biomarker of acid phosphatases to determine osteoclastic activity encounter problems in specificity, sensitivity, complicated measurements and measuring time.

In general, the assay of TRACP 5b activity can be performed by using a phosphoric acid ester as a synthetic substrate in the presence of tartrate and colorimetrically measuring the end product (alcohol or phenol) produced by the enzymatic reaction. In this assay, the tartarate inhibits prostate-derived acid phosphatase. Thus, the activity of acid phosphatase remaining is measured on the substrate and then, the TRACP activity calculated from the measurements is regarded to be the TRACP 5b activity. However, this method is not very specific, since tartrate inhibits other acid phosphatases originating from erythrocytes and platelets present in serum samples and the method includes these other acid phosphatases, in addition to the osteoclast-derived acid phosphatase. In order to improve the method above, it was proposed to pretreat serum by incubation of its 5-fold dilution at 37° C. for an hour and then measure the TRACP activity in the presence of tartrate using p-nitrophenyl phosphate (pNPP) as a substrate (NICHIDAI-ISHI, 49: 904–911, 1990; Clin. Chem., 33: 458–462, 1987). This improved method can exclude acid phosphatases derived from erythrocytes but does not exclude platelet-derived acid phosphatases. For a more specific method for assaying the activity, the present inventors previously found that there is a difference in resistance to a fluoride between TRACP 5b and erythrocyte- and platelet-derived acid phosphatases, and reported a method for determination of TRACP 5b based on this difference in resistance (JP 10-37198A). This method could eliminate any influence of erythrocyte- and platelet-derived tartrate-resistant acid phosphatases but was still affected by TRACP 5a. The method requires determination of the TRACP 5b activity by measuring the total tartrate-resistant acid phosphatase activity, and then calculating the difference between the total activity and the activity not inhibited in the presence of a fluoride. Therefore, a further improvement is desired in view of sensitivity. Another method reported involves use of an additional TRACP 5b inhibitor in the aforesaid method using a fluoride to determine the TRACP 5b activity more specifically (JP 2001-231595A). The method using a fluoride alone is more specific but a problem still remains in accuracy because the osteoclast-derived TRACP 5b activity is assayed based on the difference calculated, as in other known methods.

On the other hand, the following methods using a polyclonal antibody or a monoclonal antibody are also known for immunoassay methods to assay the TRACP 5b activity (J. Clin. Endocrinol. Metab., 71: 442–451, 1990; J. Bone Miner. Res., 13: 683–687, 1998; Immunol. Lett., 70: 143–149, 1999; J. Bone Miner. Res., 14: 464–469, 1999; Clin. Chem., 45: 2150–2157, 1999; Clin. Chem., 46: 1751–1754, 2000). In these methods, an influence of TRACP 5a is not negligible because TRACP 5a and TRACP 5b are both measured undesirably without discriminating from one another. An immunoassay for measuring TRACP 5b more specifically is reported also in WO 99/50662 and JP2002-510050A. While this method is more specific to the TRACP 5b activity, the antibody used for the immunoassay is not specific to TRACP 5b and is also reactive with TRACP 5a. The TRACP 5b activity should be assayed by calculation from the measurement data in the immunoassay, taking advantage of the difference in optimum pH between TRACP 5b and TRACP 5a. For this reason, it is a concern that inaccurate assay data may result from increased TRACP 5a levels in specimens from patients with terminal renal failure. Furthermore, the difference between normal specimens and pathologic specimens with accelerated bone resorption is so small that the sensitivity required for a bone resorption marker is not obtained (Clin. Chim. Acta, 301: 147–158, 2000).

SUMMARY OF THE INVENTION

In view of the foregoing problems, the present invention aims at providing a monoclonal antibody specific to an osteoclast-derived tartrate-resistant acid phosphatase (TRACP 5b) functioning as a marker for bone resorption, a hybridoma capable of producing the monoclonal antibody, a method of detecting TRACP 5b using the monoclonal antibody and a kit for use in the method.

The present invention relates to a monoclonal antibody to TRACP 5b, which provides a higher reactivity with tartrate-resistant acid phosphatase 5b (TRACP 5b, also called osteoclast-derived tartrate-resistant acid phosphatase) than that with tartrate-resistant acid phosphatase 5a (TRACP 5a) and has a higher specificity to TRACP 5b.

The present invention further relates to a hybridoma capable of producing the monoclonal antibody described above.

Furthermore, the present invention relates to a method of detecting TRACP 5b, which comprises detecting TRACP 5b according to an immunoassay using the monoclonal antibody described above.

Still further, the present invention relates to a kit for use in the detecting method, comprising the monoclonal antibody described above.

DESCRIPTION OF THE PREFERRED EMBODIEMNTS

Figure 1:
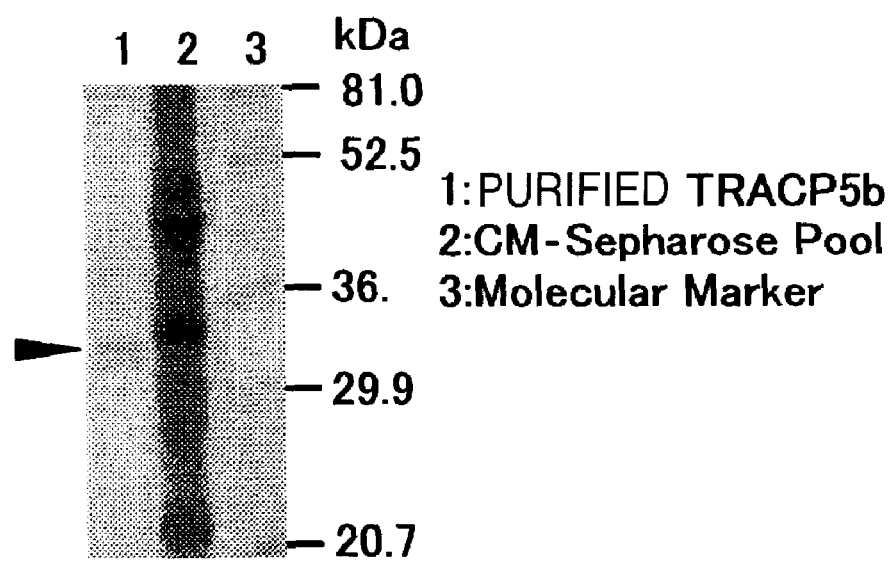
FIG. 1 shows the results of analysis of TRACP 5b isolated and purified from human femoral caput by SDS-PAGE.

The monoclonal antibody of the invention can be acquired by using as an immunogen TRACP 5b purified from human osteoclast cells. In the embodiments described below, TRACP 5b purified from normal osteoclast cells was used as an immunogen for immunization; not only the purified TRACP 5b but TRACP 5b from osteoclastic tumor may also be used as an antigen.

The monoclonal antibody of the invention can be produced from the hybridoma acquired by immunizing an animal using, e.g., purified human TRACP 5b as an antigen and fusing anti-human TRACP 5b antibody-producing cells produced in the animal to myeloma cells.

The hybridoma can be produced by the following procedures. That is, human TRACP 5b acquired as described above is mixed with known adjuvant such as Freund's complete or incomplete adjuvant, aluminum hydroxide adjuvant, pertussis adjuvant, etc. to prepare an adjuvant solution for sensitization, which is administered to an animal such as mice or rats, intraperitoneally, subcutaneously or via the tail vein, in several doses every 1–3 weeks. An amount of the antigen is between 1 µg to 100 mg, preferably about 50 µg. In general, immunization is performed 2 to 7 times, and various methods are known to effect the immunization. Next, antibody-producing cells derived from spleen, etc. are fused to cells such as myeloma cells that can grow in vitro. The antibody-producing cells can be acquired from the spleen, etc. of mice, nude mice, rats, etc.

The fusion above can be carried out in accordance with the known method established by Koehler and Milstein (Nature, 256, 495, 1975) using polyethylene glycol (PEG). The fusion may also be carried out through electrofusion using Sendai virus.

The hybridomas capable of producing the antibody, which can recognize human TRACP 5b, are selected from the fused cells described above. The selection proceeds as follows. After fusion, the resulting hybridomas are maintained in HAT medium and HT medium, cloned by limiting dilution and selected in the colonies produced from the maintained cells. When antibodies to human TRACP 5b are contained in the culture supernatants of the colonies produced from the fused cells plated on a 96-well plate, etc., the supernatants are placed on human TRACP 5b-immobilized assay plates. Following the reaction, clones capable of producing the monoclonal antibody can be screened by ELISA, which involves reacting a labeled secondary antibody such as anti-mouse-immunoglobulin HRP-labeled antibody. For labeling the antibody, a label including an enzyme such as alkaline phosphatase, a fluorescent material, a radioactive substance, etc. can be used, in addition to HRP. For control, ELISA is simultaneously performed on the assay plates coated only with BSA as a blocking agent, thereby to screen human TRACP 5b-specific antibodies. In short, clones which are positive on the human TRACP 5b-coated plates and negative by ELISA using BSA can be screened for.

Of the hybridomas which produce monoclonal antibodies capable of recognizing human TRACP 5b, preferred examples of the hybridomas are hybridomas producing the monoclonal antibodies, which are reactive particularly with human TRACP 5b and are not cross-reactive with erythrocyte-, platelet-, neutrophil- and prostate-derived acid phosphatases. One example is hybridoma Trk62 established by the present inventors.

For the monoclonal antibodies of the invention, monoclonal antibodies having a higher affinity to human TRACP 5b than to human TRACP 5a are particularly preferred and those showing a higher reactivity with human TRACP 5b by twice or more than the reactivity with human TRACP 5a in the detection system are more preferred, since the test results reflect bone resorption more clearly when they are used for clinical tests. An example of such hybridomas is hybridoma Trk62 established by the inventors. Hybridoma Trk62 has been internationally deposited under the Budapest Treaty on Feb. 14, 2002, at National Institute of Advanced Industrial Science and Technology, International Patent Organism Depositary, under the accession number of FERM BP-7890.

The hybridomas described above are cultured in medium conventionally used for cell culture, e.g., α-MEM, RPMI1640, ASF, S-clone, etc., to recover the monoclonal antibody from the culture supernatants. The monoclonal antibody may also be produced by the procedure which involves intraperitoneally injecting the cells into pristane-primed animals or nude mice of the hybridoma origin to retain the ascites fluid, and collecting and purifying the retained ascites fluid to recover the monoclonal antibody.

For recovering the monoclonal antibody from the supernatants or ascites fluids described above, conventional methods are available. Examples of the conventional methods are salting out with ammonium sulfate, sodium sulfate, etc.; chromatography, ion exchange chromatography, affinity chromatography using protein A, protein G, etc.

The monoclonal antibody of the invention thus acquired is more highly reactive with TRACP 5b than with TRACP 5a, and more specific to TRACP 5b than to TRACP 5a. Specifically, the monoclonal antibody of the invention has a higher reactivity with TRACP 5b by twice or more than the reactivity with TRACP 5a. More specifically, the monoclonal antibody has a higher reactivity with TRACP 5b by twice or more than the reactivity with TRACP 5a, when TRACP 5a and 5b of an equal activity are reacted with the monoclonal antibody, respectively. Still more specifically, when TRACP 5a and TRACP 5b, which show the enzymatic activity of 10 U/L in the reaction at pH 5.7 (i.e., pH 5.7 is where TRACP 5a and TRACP 5b show the same enzymatic activity) in the presence of tartaric acid or a tartrate using p-nitorophenylphosphate (pNPP) substrate, are reacted with the monoclonal antibody of the invention immobilized on a plate, and the respective enzymatic activities of TRACP 5a and TRACP 5b conjugated to the antibody are measured at pH 6.1 (i.e., optimal pH value of TRACP 5b) in the presence of tartaric acid or a tartrate using the above pNPP substrate, the monoclonal antibodies having a higher reactivity with TRACP 5b by twice or more, preferably 3 times or more, than the reactivity with TRACP 5a, are particularly preferred, as will be clearly indicated in the description of EXAMPLE 1 (8) of a specificity assay.

Moreover, as will also be clearly demonstrated in the description of EXAMPLE 1 (8) of a specificity assay, the monoclonal antibody of the invention does not show any substantial cross-reactivity with erythrocyte-, platelet-, neutrophil- and prostate-derived acid phosphatases. Furthermore, the monoclonal antibody of the invention can recognize the steric structure of TRACP 5b retained in the native enzyme form, which will be clearly demonstrated in the description in EXAMPLE 1 (7) of Western blotting and EXAMPLE 4.

The monoclonal antibody of the invention enables to specifically detect TRACP 5b in a sample with high sensitivity. Samples of interest include blood, serum, plasma, tissues such as bone, etc.

In the method for detection of TRACP 5b according to the invention, TRACP 5b in a sample can be detected by, for example, an immunoassay utilizing the determination of the enzymatic activity of TRACP 5b, a sandwich ELISA or a tissue immunostaining assay.

The immunoassay utilizing the determination of the enzymatic activity of TRACP 5b includes a method wherein TRACP in a sample such as serum is bound to the monoclonal antibody of the invention, the bound TRACP 5b is reacted with an enzyme substrate of TRACP 5b such as p-nitrophenyl phosphate, and the enzymatic activity of the bound TRACP 5b is thus determined. More specifically, in such method, the sample containing TRACP 5b is added to the monoclonal antibody of the invention immobilized on a solid phase support, so that TRACP 5b in the sample is subjected to an antigen-antibody reaction and TRACP 5b is thus bound to the antibody immobilized on the solid phase support. Then, the solid phase support is washed to remove other components of the sample which have not been bound to the antibody. Thereafter, the enzyme substrate of TRACP 5b such as p-nitrophenyl phosphate or its salt is added to the reaction system, and the substrate is reacted with the TRACP 5b bound to the antibody. After the enzymatic reaction is terminated with a reaction terminating solution, a component such as p-nitrophenol resulting from the enzymatic reaction is determined by measuring the absorbance at wavelength of 390 nm to 450 nm, preferably 400 nm to 430 nm. The absorbance is indicative of the enzymatic activity of TRACP 5b, and TRACP 5b in the sample is therefore determined.

As seen from the above, the antibody of the invention is preferably used as an antibody immobilized on a solid phase support. Any solid phase supports conventionally used in a solid phase immunoassay such as ELISA may be used in the method of the invention without limitation. The solid phase support may be made from polystyrene, polypropylene, polycarbonate, polyethylene, nylon, polymethacrylate and the like. The support may be in the form of a plate or beads.

The antibody immobilized on the solid phase support may be prepared by binding directly or indirectly the antibody to the support through physical or chemical binding or affinity. The amount of the antibody sensitized is generally in the range of 1 ng/ml to 100 mg/ml.

For performing the method, a kit may be used containing a solid phase support, the monoclonal antibody of the invention and an enzyme substrate of TRACP 5b. In the kit, the solid phase support and the antibody may be provided separately from each other, and the antibody may be immobilized on the support just prior to use. Alternatively, the antibody may have been immobilized on the support previously. The kit may contain a washing solution for removing from the support other unbound components in the sample after TRACP 5b has been bound to the support. An amount of the antibody sensitized is generally in the range of 1 ng/ml to 100 mg/ml. The washing solution includes Tris buffer containing surface active agents. The kit may preferably contain a reaction terminating solution including an aqueous alkaline solution such as aqueous sodium hydroxide and potassium hydroxide solutions. Further, the kit may, if necessary, contain a dilution solution for the sample including buffer solutions such as Tris buffer. The buffer solution may, if necessary, contain a chelating agent such as EDTA.2Na and an inorganic salt such as NaCl.

In the method of the invention, TRACP 5b in a sample is detected according to a sandwich ELISA using the monoclonal antibody of the invention. In the ELISA, an antibody other than that of the invention is used. Specifically, the antibody of the invention as a primary antibody is immobilized on a solid phase support such as a plate, and then TRACP 5b in a sample such as serum is reacted with the immobilized antibody, followed by washing of the support. Thereafter, TRACP 5b bound to the support is reacted with a secondary antibody such as a biotinated other monoclonal antibody, polyclonal antibody or antiserum specific for TRACP 5b, followed by the reaction with peroxidase-labeled streptoavidine. Then, a peroxidase enzymatic reaction is carried out followed by a coloring reaction, whereby TRACP 5b in the sample is detected. Antibodies labeled with enzymes such as peroxidase and alkaline phosphatase may be used as the secondary antibody. Alternatively, antibodies labeled with radioisotope, fluorescent compound, magnetic compound or colloid may be used as the secondary antibody.

The sandwich ELISA may be carried out using a kit containing a solid phase support, a monoclonal antibody of the invention, a labeled antibody other than that of the present invention which is specific for TRACP 5b, and components for detecting the labeled antibody. When the label is biotin, the components for detecting the labeled antibody may be peroxidase-labeled streptoavidine, or tetramethylbenzidine as a substrate for the peroxidase and hydrogen peroxide. When the label is alkaline phophatase, the components may be reagents containing p-nitrophenyl phosphate. The kit may, if necessary, contain a washing solution.

In the invention, the presence of TRACP 5b in a sample can be detected by a tissue immunostaining assay using the monoclonal antibody of the invention. For example, a frozen sample is prepared from, for example, human osteoclast cell tissue according to the conventional manner, and the monoclonal antibody of the invention is reacted therewith. The reaction product is then reacted with a secondary antibody labeled with, for example, an enzyme such as an alkaline phosphatase, followed by the coloring reaction for observation. In this fashion, the presence of TRACP 5b can be detected specifically.

Kits suitable for use in the detection method may include the monoclonal antibody as a primary antibody, a labeled secondary antibody and reagents for staining the labeled secondary antibody. The reagents for staining the antibody may contain chromogenic substrates.

Hereinafter the invention will be described in more detail, with reference to the following preferred embodiments, but the invention is not deemed to be limited only to these EXAMPLES.

EXAMPLE 1

Production of Monoclonal Antibody Highly Specific to Osteoclast-Derived Tartrate-Resistant Acid Phosphatase (TRACP 5b) and its Properties (1) Purification of TRACP 5b After informed consent was obtained, 130 g of human femoral caput surgically dissected was frozen in liquid nitrogen followed by pulverizing with a hammer. The resulting powders were suspended in 200 mL of buffer solution (50 mM Tris-HCl, 0.3 M KCl, pH 7.5) containing a protease inhibitor, etc. and the suspension was homogenized by a ultrasonic homogenizer. After stirring at 4° C. overnight, centrifugation was conducted at 10,000 rpm for 20 minutes. The supernatant was dialyzed to 10 mM Tris buffer (pH 8.2), and the dialysate was passed through CM-Sepharose Column (Sigma Inc.). The protein adsorbed was eluted on a linear gradient of the Tris buffer containing NaCl. The tartrate-resistant acid phosphatase activity was assayed using pNPP substrate, and fractions having a high activity were pooled. After condensation, the condensate was dialyzed to 20 mM Tris buffer, pH 7.2, containing 0.7 M NaCl and the dialysate was passed through Superdex 200 Column (Amersham Pharmacia Inc.). The tartrate-resistant acid phosphatase activity in the eluate was assayed as above and the active fractions were pooled. The pooled fractions were applied to HiTrap Heparin HP Column (Amersham Pharmacia, Inc.) to elute the adsorbed protein on a linear gradient of the 20 mM Tris buffer, pH 7.4, containing NaCl. The highly active tartrate-resistant acid phosphatase fractions were pooled and concentrated to give 0.4 mg of purified TRACP 5b. The amount of protein was determined by $A_{280}$, and after SDS-PAGE (TIFCO) followed by silver staining, the protein was purified until it showed a single band having a molecular weight of about 35,000. Thus, the protein was identified to be TRACP 5b (FIG. 1). The enzyme purified to a single band was used as purified TRACP 5b immunogen.

(2) Immunization of Mice with Purified Human TRACP 5b

Purified human TRACP 5b was diluted to 250 μg/ml with 50 mM citrate buffer (pH 5.5) and an aliquot of 25 μg (100 μl) was taken and thoroughly mixed with 100 μl of Freund's complete adjuvant (Wako Pure Chemical Industries, Ltd.) until the mixture was emulsified. The emulsified suspension prepared was intraperitoneally injected into Balb/c female mice 6 weeks old (CLEA Japan, Inc.) under diethyl ether anesthesia. After 2 weeks, an equal amount of TRACP 5b (25 μg/ml) was mixed with Freund's incomplete adjuvant (Wako Pure Chemical Industries, Ltd.) until the mixture became emulsified suspension, in the same manner as with Freund's complete adjuvant, followed by immunization to mice. Then the same procedures were repeated at biweekly intervals. For the fourth booster, 25 μg/ml of TRACP 5b in 50 mM citrate buffer (pH 5.5) was given intravenously through the mice tail for final immunization.

(3) Establishment of Hybridomas

Three days after the final immunization, the spleen surgically dissected from the TRACP 5b-immunized mice under diethyl ether anesthesia was aseptically dispersed to prepare splenocytes. The cell fusion was carried out according to the method of Kohler and Milstein (Nature, 256: 495, 1975), and the splenocytes were fused to myeloma cells P3-X63-Ag8-U1 (P3U1) using polyethylene glycol (PEG 4000) (Merck, Inc.). The fusion of TRACP 5b was made between $2 \times 10^7$ of myeloma cells P3-X63-Ag8-U1 (P3U1) and $8 \times 10^7$ of the splenocytes, indicating that the fusion ratio of myeloma cells to splenocytes was approximately 4:1. The fused cells were dispersed in 10% FCS (INVITROGEN, Inc.)-containing α-MEM (IRVINE, Inc.) HAT (Cosmobio Co., Ltd.) medium, dispensing the suspension onto 96-well microtiter culture plates (Sumitomo Bakelite Co., Ltd.) and culturing at 37° C. in 5% $CO_2$.

(4) Screening of Colonies

After approximately 2 weeks, it was confirmed that colonies were grown and ready for screening. The screening protocols performed are described below.

To prepare plates for screening, TRACP 5b purified in (1) above was dissolved in 50 mM citrate buffer. The solution was dispensed into 96-well microtiter plates (Nunc, Inc.) in an amount of 0.5 μg/100 μl/well. The plates were allowed to stand at 4° C. for 2 nights followed by washing 3 times with Tris buffer containing 0.05% Tween 20 (Wako Pure Chemical Industries, Ltd.). Then a 200 μl aliquot of 1.5% BSA (SIGMA, Inc.) solution was dispensed on each well to block non-specific reactions, which was further allowed to stand at 4° C. overnight. After the plates obtained were washed 3 times with Tris buffer containing 0.05% Tween 20, 100 μl of the culture supernatant of hybridoma obtained in (3) above was reacted therewith. Further washing was followed by addition of a secondary antibody, i.e., HRP-conjugated anti-mouse immunoglobulin antibody (Zymed, Inc.). After washing, 100 μl of a citrate solution containing 3 mg/ml of o-phenylenediamine (OPD)(Nakarai Co., Ltd.) as a chromogenic substrate for HRP was added to the mixture and allowed to stand for a given period of time for color formation. To terminate the reaction 100 μl of 1N sulfuric acid (Wako Pure Chemical Industries, Ltd.) was further added to the mixture, and absorbance was measured at a measuring wavelength of 492 nm. The clones that turned positive as described above were re-cloned by limiting dilution and the supernatant was monitored again.

(5) Identification of Antibody

By confirming the reactivity of the clones with purified TRACP 5b by ELISA, clones Trk62 and Trk49 reactive with the purified TRACP 5b-coated plates were acquired. The monoclonal antibody Trk62 produced by clone Trk62 showed a strong reactivity with the purified TRACP 5b, whereas monoclonal antibody Trk62 did not react with BSA-coated plates. On the other hand, the monoclonal antibody Trk49 produced by clone Trk49 showed a weak reactivity with the purified TRACP 5b. The above antibodies Trk62 and Trk49 were assayed on a monoclonal antibody typing kit (Amersham Pharmacia, Inc.) and found to have the following properties.

| Class | Subclass | Light Chain |
|-------|----------|-------------|
| IgG   | IgG1     | κ           |

(6) Production and Purification of Monoclonal Antibody

Hybridoma Trk62 obtained in (4) above was intraperitoneally administered in a dose of $1\times10^7$ cells to Balb/c mice (CLEA Japan, Inc.)(10 weeks old, female) 2 weeks after priming with 0.5 ml of pristane (Aldrich, Inc.). The ascites fluids retained in the ascites cavities of mice were surgically collected under diethyl ether anesthesis. The collected ascites fluid was used as a sample and serially diluted. The ascites fluid dilution was monitored by ELISA in the same manner as used in the procedures for screening of the colonies in (4) described and found that the dilution contained a high level of the monoclonal antibody. This ascites fluid was treated with 40% ammonium sulfate and dialyzed to PBS. The dialysate was purified through Protein G Column (Amersham Pharmacia, Inc.) and confirmed on SDS-PAGE. Thus, the monoclonal antibody Trk62 was found to have a single band at a molecular weight of about 150,000 under non-reducing conditions and and 2 bands at molecular weights of about 50,000 and about 25,000 under methanol-reducing conditions. The purified monoclonal antibody yield was about 15 mg per mouse, which was sufficient for industrial application. Similarly, the monoclonal antibody Trk49 was obtained from the hybridoma Trk49. The hybridoma Trk49 has been internationally deposited under the Budapest Treaty on Nov. 27, 2002, at National Institute of Advanced Industrial Science and Technology, International Patent Organism Repositary, under the accession number of FERM BP-8249.

(7) Western Blotting

Based on the results of western blotting, etc., it was found that monoclonal antibody Trk62 did not recognize SDS-treated TRACP 5 but recognized native TRACP 5, which is described below in detail.

Figure 2:
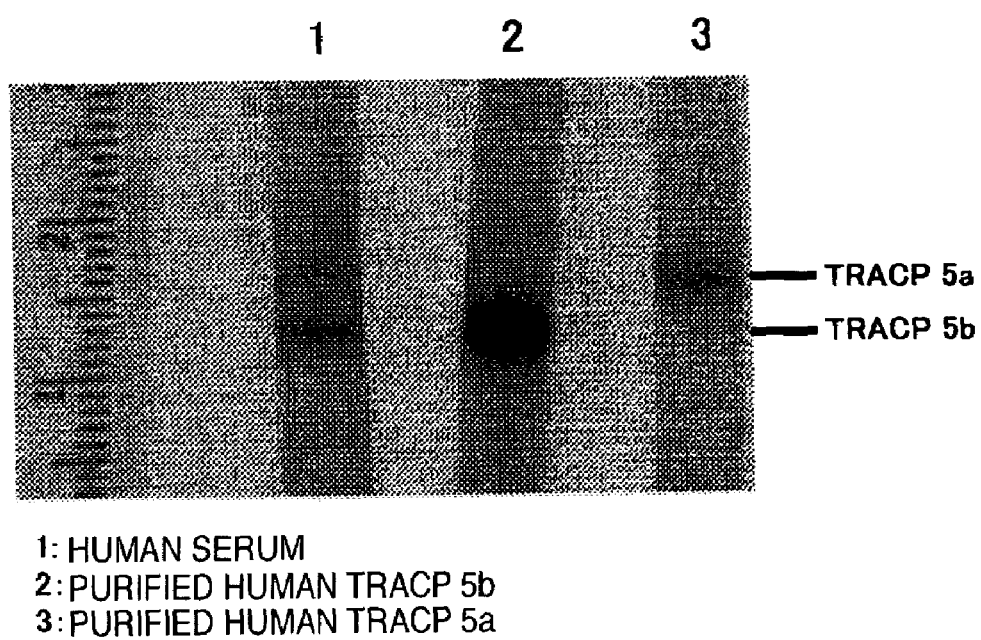
FIG. 2 shows the results of analysis of TRACP 5a and TRACP 5b purified from human cord blood by disc electrophoresis.
Figure 3:
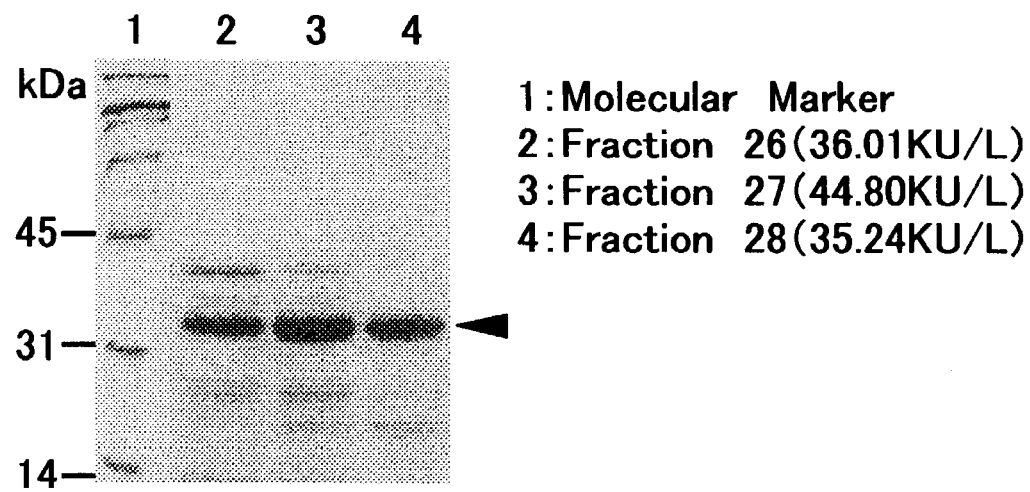
FIG. 3 shows the results of analysis of recombinant TRACP produced from host insect cells by SDS-PAGE.
Figure 4:
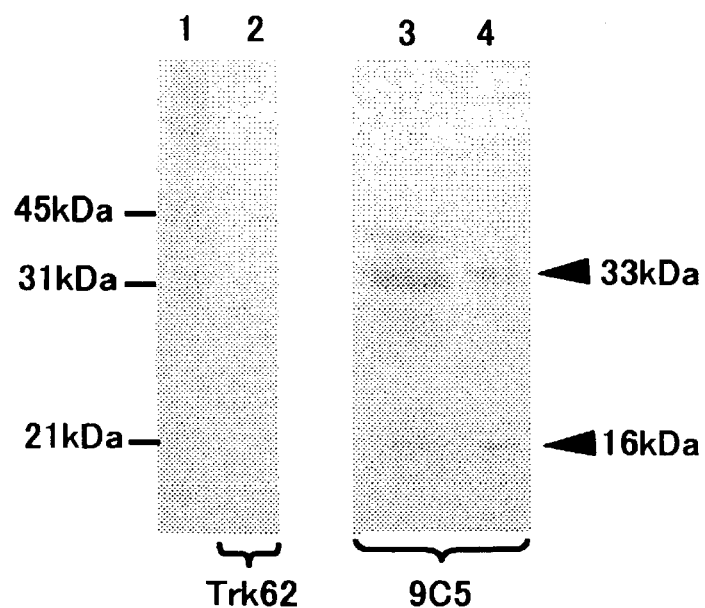
FIG. 4 shows the results of analysis for the reactivity of anti-TRACP monoclonal antibody 9C5 used as a positive control with human TRACP 5a, TRACP 5b and recombinant TRACP, by western blotting.

After obtaining informed consent, TRACP was purified from human cord blood in accordance with the method already known (Clin. Chem., 24:7, 1105–1108, 1978) and used as samples for western blotting. Upon the purification, human TRACP was separated into 2 isoforms, TRACP 5a and TRACP 5b. TRACP 5a and TRACP 5b were identified by disc electrophoresis (Clin. Chem., 24:2, 309–312, 1978 (FIG. 2) and by an activity assay using a fluoride as an inhibitor (Clin. Chem., 46:4, 469–473, 2000). Separately, human recombinant TRACP (Baculoviral rhTRACP) was produced using insect cells by modifying the method of Hyman, et al. (J. Biol. Chem., 269, 1294–1300, 1994) already known in the art, purified and then used as antigens (Fractions 26, 27 and 28 shown in FIG. 3 were pooled and used). From each of the three enzyme proteins (human TRACP 5a, TRACP 5b and Baculoviral rhTRACP), 2 μg was taken and subjected to SDS-PAGE under non-reducing conditions. Monitoring of the Trk62 reactivity by western blotting reveals that Trk62 did not react with any of human TRACP 5a, TRACP 5b or Baculoviral rhTRACP. However, anti-TRACP monoclonal antibody 9C5 (Zymed, Inc.)(Hybridoma, 16: 175–182, 1997; BioTec. Histochem., 73:316–324, 1998) used as a positive control reacted with 33 kDa human TRACP 5a, TRACP 5b and Baculoviral rhTRACP and with a small fragment of 16 kDa, which fragment was observed in all three antigens (FIG. 4). It is already known that anti-TRACP monoclonal antibody 9C5 reacts with the small fragment of 16 kDa modified by thermal degeneration (Hybridoma, 16: 175–182, 1997 Biotech. Histochem., 73: 316–324, 1998).

The results reveal that surfactant SDS changed the steric structures of human TRACP 5a, TRACP 5b and Baculoviral rhTRACP and because of the absence of detectable steric structures, the monoclonal antibody Trk62 of the invention lost its reactivity with human TRACP 5a, TRACP 5b and Baculoviral rhTRACP. This is because Trk62 is a monoclonal antibody which recognizes the steric structures of human TRACP 5a, TRACP 5b and Baculoviral rhTRACP. The results also reveal that monoclonal antibody Trk62 recognizes the native structure of TRACP.

(8) Specificity Assay

The monoclonal antibody Trk62 was tested for specificity by the following procedures. The assay method comprises steps (i) through (v) below.

(i) Anti-mouse immunoglobulin (DAKO Japan) was dispensed to the microtiter plates (Nunc, Inc.) used for the screening of colonies in (4) above in 1 μg/100 μl/well. The plates were allowed to stand at 4° C. for 2 nights. Then, the plates were washed 3 times with 0.05% Tween 20-containing Tris (SIGMA, Inc.) buffer and 200 μl aliquot of 1.5% BSA (SIGMA, Inc.) solution was dispensed into the plates to block non-specific reactions. The plates were further allowed to stand at 4° C. overnight.

(ii) The plates thus completed were washed 3 times with 0.05% Tween 20-containing Tris buffer and reacted at room temperature for an hour for comparison with 400 ng/100 μl/well of monoclonal antibody Trk62 of the invention and with monoclonal antibody 01A (attached to BoneTRAP Assay Kit available from Suomen Bioanalytiikka Oy; monoclonal antibody described in WO 99/50662 and P2002-510050A). The plates were further washed 3 times with 0.05% Tween 20-containing Tris buffer.

(iii) Next, the monoclonal antibodies Trk62- and 01A-reacted plates were reacted with various acid phosphatases. The acid phosphatases used as sample were purified human TRACP 5a and Baculoviral rhTRACP used for the western blotting in (7) above, and TRACP 5b used for sensitization, erythrocyte extract, platelet extract, neutrophil extract and prostate-derived acid phosphatase (PAP) (SIGMA, Inc.). In specimens containing these ACP isoforms, the enzymatic activity of both TRACP 5a and 5b was adjusted to 10 U/L (activity level measured in 8 mM pNPP substrate solution, 0.1 M sodium acetate and 40 mM sodium tartrate, pH 5.7), and a 100 μl aliquot was added onto the antibody-bound plates.

(iv) After reacting at room temperature for an hour, the plates were washed 3 times with 0.05% Tween 20-containing Tris buffer, and 100 μl of the substrate solution (8 mM pNPP, 100 mM sodium acetate and 40 mM sodium tartrate, pH 6.1) was added thereto. The mixture was allowed to stand for an hour at 37° C. for color formation. Absorbance at 405 nm was measured and the amounts of various ACP isoforms reacted with monoclonal antibodies Trk62 and 01A, respectively, were determined. The measurement data were calculated by subtracting the blank absorbance using saline alone as a specimen from the absorbance of each specimen. The measurement data obtained are shown in TABLE 1.

TABLE 1

Amount of monoclonal antibody reacted with
ACP isoforms (absorbance at 405 nm:
absorbance obtained by subtracting the blank
absorbance)

| ACP Isoforms | Monoclonal antibody O1A for Comparison | Monoclonal antibody TrkG2 of Invention |
|---|---|---|
| Neutrophil | 0.003 | 0.002 |
| Platelet | 0.002 | 0.001 |
| Erythrocyte | 0.001 | 0.002 |
| Prostate | 0.002 | 0.001 |
| Baculoviral rhTRACP | 0.476 (75%) | 0.486 (70%) |
| TRACP 5a | 0.413 (65%) | 0.222 (32%) |
| TRACP 5b | 0.636 (100%) | 0.694 (100%) |
| TRACP 5b/TRACP 5a | 1.54 | 3.13 |

Percentage within parenthesis indicates the reactivity when absorbance of TRACP 5b was made 100%.

The results shown in TABLE 1 reveal that monoclonal antibodies O1A and Trk62 reacted only with human TRACP 5b, TRACP 5a and Baculoviral rhTRACP but did not show any cross-reactivity with other ACP isoforms, though the reaction percentage was different. That is, when the reactivity with TRACP 5b was made 100%, the reactivity of two antibodies with Baculoviral rhTRACP was about 70%. However, the reactivity of TRACP 5a with monoclonal antibody O1A was 65%, whereas the reactivity with monoclonal antibody Trk62 was only 32%. This means that monoclonal antibody Trk62 has a higher affinity for TRACP 5b. That is, the ratio in the reactivity of TRACP 5b to TRACP 5a (TRACP 5b/TRACP 5a) was 1.54 for monoclonal antibody O1A and 3.13 for monoclonal antibody Trk62, indicating that monoclonal antibody Trk62 provides a higher specificity to TRACP 5b by about two times, as compared to monoclonal antibody O1A.

Based on the foregoing results, the monoclonal antibody Trk62 of the invention has the following properties.

That is, each of TRACP 5a and TRACP 5b, which show an enzymatic activity of 10 U/L when reacted at pH 5.7 in the presence of sodium tartrate using p-nitrophenyl phosphate (pNPP) substrate, is reacted with the monoclonal antibody of the invention immobilized to the plates, and the enzymatic activity of each of TRACP 5a and TRACP 5b bound to the plates is assayed at pH 6.1 using the pNPP substrate described above. The reactivity with TRACP 5b is higher by 3.13 times than the reactivity with TRACP 5a.

EXAMPLE 2

Immunoassay Utilizing the Determination of the Enzymatic Activity of TRACP 5b and Using Monoclonal Antibody Trk62 for Clinical Samples In order to ascertain the clinical significance of monoclonal antibody Trk62 in association with bone resorption-related diseases, sera collected from patients who received hormone replacement therapy (HRT) were used as samples to determine the TRACP 5b level in the samples.

(1) Method

The assay for TRACP 5b using monoclonal antibody Trk62 was carried out by the same procedures as used for the specificity assay in EXAMPLE 1 (8), provided that the assay data was calculated by measuring recombinant TRACP attached to the BoneTRAP Assay Kit (Suomen Bioanalytiikka Oy) as a standard and converting the absorbance into U/L enzymatic activity unit based on the calibration curve thus obtained. For comparison, the biochemical assay for the total TRACP activity (Clin. Chem., 44: 221–225, 1998) and ELISA for TRACP 5b were carried out using BoneTRAP Assay without any modification. Samples were collected from the patients who gave informed consent, and stored at −80° C. until they were provided for testing. Intervals before and after HRT were 7.4 months on average.

(2) Results

The results obtained are shown in TABLE 2.

TABLE 2

Assay of TRACP 5b in clinical samples

| | Comparison Total TRACE by biochemical assay TRACP 5b (IU/L) | (%) | Comparison Monoclonall antibody O1A TRACP 5b (U/L) | (%) | This Invention Monoclona antibody Trk62 (U/L) | (%) |
|---|---|---|---|---|---|---|
| No. 1: | | | | | | |
| Before HRT | 19.8 | | 6.9 | | 1.4 | |
| After HRT | 17.6 | 88.9% | 2.6 | 37.7% | 0.5 | 35.7% |
| No. 2: | | | | | | |
| Before HRT | 28.2 | | 9.4 | | 2.4 | |
| After HRT | 21.0 | 74.5% | 6.1 | 64.9% | 1.2 | 50.0% |
| No. 3: | | | | | | |
| Before HRT | 17.7 | | 4.4 | | 1.0 | |
| After HRT | 14.6 | 82.5% | 3.4 | 77.3% | 0.5 | 50.0% |
| No. 4: | | | | | | |
| Before HRT | 2.6 | | 6.5 | | 1.5 | |
| After HRT | 19.5 | 73.3% | 4.6 | 70.8% | 0.7 | 46.7% |
| No. 5: | | | | | | |
| Before HRT | 22.3 | | 5.9 | | 0.8 | |
| After HRT | 19.5 | 87.4% | 3.5 | 59.3% | 0.5 | 62.5% |
| No. 6: | | | | | | |
| Before HRT | 24.5 | | 7.6 | | 1.1 | |
| After HRT | 17.3 | 70.6% | 4.1 | 53.9% | 0.2 | 18.2% |
| No. 7: | | | | | | |
| Before HRT | 22.9 | | 5.6 | | 1.0 | |
| After HRT | 13.4 | 58.5% | 1.5 | 26.8% | 0.0 | 0.0% |
| No. 8: | | | | | | |
| Before HRT | 21.0 | | 6.3 | | 0.9 | |
| After HRT | 15.8 | 75.2% | 3.3 | 52.4% | 0.2 | 22.2% |
| No. 9: | | | | | | |
| Before HRT | 24.7 | | 6.1 | | 1.4 | |
| After HRT | 21.6 | 87.4% | 4.2 | 68.9% | 0.8 | 57.1% |
| No. 10: | | | | | | |
| Before HRT | 21.9 | | 6.1 | | 1.0 | |
| After HRT | 16.1 | 73.5% | 3.1 | 50.8% | 0.1 | 10.0% |
| No. 11: | | | | | | |
| Before HRT | 24.3 | | 7.7 | | 0.8 | |
| After HRT | 15.9 | 65.4% | 3.9 | 50.6% | 0.5 | 62.5% |
| No. 12: | | | | | | |
| Before HRT | 21.0 | | 4.0 | | 0.3 | |
| After HRT | 16.3 | 77.6% | 2.5 | 62.5% | 0.0 | 0.0% |
| No. 13: | | | | | | |
| Before HRT | 23.3 | | 6.5 | | 1.4 | |
| After HRT | 20.1 | 86.3% | 3.7 | 56.9% | 0.3 | 21.4% |
| Average ratio in post-therapy | | 77.0% | | 56.4% | | 33.6% |

Ideal agents for clinical tests are those giving test data that decrease after HRT dynamically as compared to the data in the pre-therapy group. Then, therapeutic effects can be assessed precisely. Therefore, when the test data obtained in the post-therapy are the smallest possible value as compared to the data before therapy, such agents are suitable for use in clinical tests. Reviewing the results shown in TABLE 2, the test data in the post-therapy group for assessing the therapeutic effects by ELISA using monoclonal antibody Trk62 acquired in EXAMPLE 1 indicated 33.5% on average based on the data before therapy, indicating a very large rate of change. These results proved more useful than those for comparison, i.e., the biochemical total TRACP assay indicating 77.0% and the BoneTRAP Assay for measuring TRACP 5b indicating 56.4%.

For comparison, TRACP 5b in the same samples was also assayed using conventional bone metabolism markers. The results were 80.5% for B-ALP (Osteolink [BAP], which measures serum bone-specific alkaline phosphatase by ELISA), 57.5% for NTx (Osteomark NTx, which measures urinary N-telopeptide of type I collagen degradation by ELISA), 68.5% for Pyr (total pyridinoline in urine on HPLC), 52.8% for D-Pyr (total deoxypyridinoline in urine on HPLC) and 77.8% for D-Pyr (Osteolink [DPD], which measures free deoxypyridinoline in urine by ELISA).

The results above reveal that TRACP 5b using monoclonal antibody Trk62 of the invention provides a larger rate of change before and after HRT than any one of the tested conventional markers of bone metabolism and is very useful from a clinical aspect.

EXAMPLE 3

Immunoassay of TRACP 5b in Serum from Adults and Infants at pH of 5.65 Using Monoclonal Antibody Trk62

The level of TRACP 5b in serum from adults having stable bone resorbing ability and infants showing vigorous bone resorption was assayed by using the monoclonal antibody of the invention.

(1) Method

The assay was carried out by the same manner as used in EXAMPLE 2 except that the pH of substrate pNPP was changed from 6.1 to 5.65. For comparison, TRACP 5b was determined by BoneTRAP Assay using the above monoclonal antibody O1A. Two sera each collected from the adults and children who gave informed consent were used as samples. It is said that TRACP 5b responsible for bone resorption provides a higher value in the infant serum because of vigorous bone metabolism.

(2) Results

The results obtained are shown in TABLE 3.

TABLE 3

Assay of TRACP 5b in serum from infant and adult (absorbance at 405 nm: value obtained by subtracting the blank value)

|  | Comparison Monoclonal antibody O1A | This Invention Monoclonal antibody Trk62 |
| --- | --- | --- |
| Child sample #1 | 0.947 | 0.379 |
| Child sample #2 | 0.552 | 0.180 |
| Mean value in | 0.750 | 0.280 |

TABLE 3-continued

Assay of TRACP 5b in serum from infant and adult (absorbance at 405 nm: value obtained by subtracting the blank value)

|  | Comparison Monoclonal antibody O1A | This Invention Monoclonal antibody Trk62 |
| --- | --- | --- |
| child samples |  |  |
| Adult sample #1 | 0.588 | 0.069 |
| Adult sample #2 | 0.623 | 0.057 |
| Mean value in Adult samples | 0.606 | 0.063 |
| Ratio of the child group to the adult group | 1.24 | 4.44 |

As noted from TABLE 3, the ratio in assay value for TRACP 5b of the child group to the adult group is 4.44 times when monoclonal antibody Trk62 was used, and is larger than 1.24 times assayed on BoneTRAP Assay Kit. Further, in the assay at pH of 5.65, bone absorption is reflected on TRACP 5b with a much better sensitivity than in the comparison, wherein the assay was made around the optimum pH of 6.1 for TRACP 5b. It is said that infant samples give higher assay values of TRACP 5b reflecting bone absorption, since bone metabolism is vigorous in infant samples.

EXAMPLE 4

Sandwich ELISA of TRACP 5b in Serum Samples from Normal Adults and Normal Infants TRACP 5b in each of the samples was quantitatively detected according to a sandwich ELISA using the monoclonal antibody Trk62 of the invention and the monoclonal antibody Trk49 which is outside the invention.

(1) Method

The monoclonal antibody Trk62 was dispensed to solid phase plates in 1 µg/µL, and allowed to stand at 4° C. for 2 days, whereby the antibody-immobilized plates were prepared, followed by blocking. After the plates were washed three times with 0.05% Tween 20-containing Tris buffer, 50 µl of the serum sample and 500 µl of citrate buffer were separately added to the plates, and allowed to stand at room temperature for one hour, whereby TRACP 5b in the samples was bound to the antibody immobilized on the plates. After washing, 100 µl of a solution of a horseradish peroxidase-conjugated antibody Trk49 as the secondary antibody was added to the remaining TRACP 5b bound to the antibody immobilized on the plate, and reacted with the remaining TRACP 5b on the plate to form sandwich complexes. After three times washing, 3 mg/mL of OPD (NAKALAI, Inc.) was added as a chromogenic substrate for the horseradish peroxidase. After a predetermined period, 1N sulfuric acid as a stop solution was added to terminate the reaction. Then, the absorbance at wavelength of 490 nm was measured for the samples. Thus, the measured absorbance value (OD) was converted to the concentration of TRACP 5b in the samples according to a standard curve previously prepared using purified TRACP 5b.

(b) Results

TABLE 4 shows results obtained from the sandwich ELISA for six serum samples of normal adults and six serum samples of normal children. The average concentration of TRACP 5b for six serum samples of normal adults was 9.92 ng/mL, whereas the average was 34.00 ng/mL for normal children which were active in bone absorption.

Those results indicate that the sandwich ELISA according to the invention accurately and correctly reflects the active bone absorption.

TABLE 4

Results from Sandwich ELISA for TRACP 5b

| Normal adults (ng/mL) | Normal children (ng/mL) |
| --- | --- |
| 7.66 | 23.60 |
| 9.74 | 17.31 |
| 10.00 | 45.55 |
| 11.16 | 37.46 |
| 9.24 | 53.39 |
| 11.71 | 26.70 |
| average 9.92 | average 34.00 |

EXAMPLE 5

Tissue Immunostaining Assay of TRACP 5b Using Monoclonal Antibody Trk62

(1) Method

Frozen human osteoclastoma tumor tissue thinly sliced at a thickness of 2 μm was treated with acetone at −20° C. to fix the tissue. After washing, the tissue samples were treated with 3% hydrogen peroxide aqueous solution for endogenous peroxidase treatment. Paraffin-embedded sections of the same sample were cut on a microtome and treated 3 times in xylene each for 5 minutes for complete deparaffinization. The samples were then rehydrated by passing them through a graded alcohol solution from 100% to 50% ethanol descending by 10% in 6 steps and microwaved with 50% citrate buffer (pH 6.0) for infiltration. Thereafter, the frozen sections and the paraffin sections were both reacted in the same way. That is, after blocking with 50 mM citrate buffer (pH 6.0) containing 5% BSA, the sections were washed and reacted at room temperature for 2 hours with monoclonal antibody Trk62, which was purified from the ascites fluid and diluted to 10 μg/ml in 50 mM citrate buffer (pH 6.0) containing 5% BSA. For positive control, anti-TRAP antibody 9C5 (ZYMED, Inc.) used in the western blotting test was reacted. After washing was performed 5 times, the sections were incubated for another hour at room temperature with a secondary antibody using ENVISION Kit (DAKO Japan, Inc.). The sections were then washed further 5 times and stained with DAB chromogen kit (DAKO Japan, Inc.). Washing was followed by microscopic observation.

(2) Results

Figure 5:
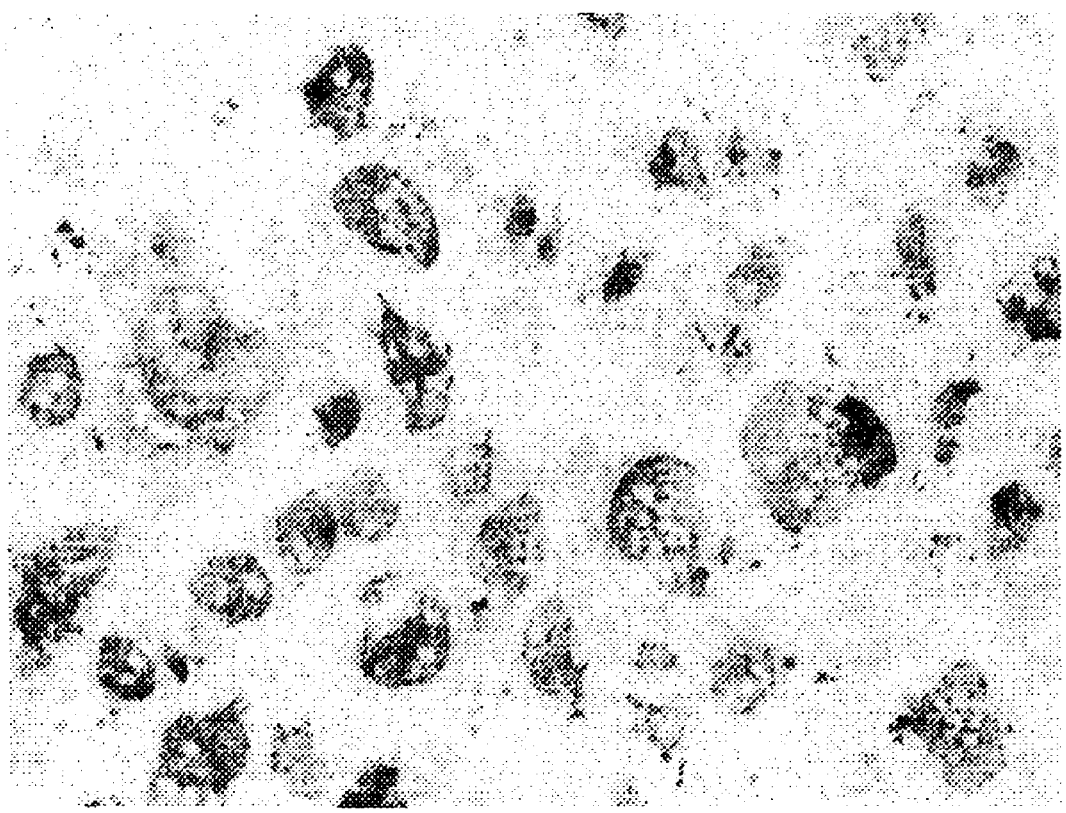
FIG. 5 shows the results of microscopic observation after reacting monoclonal antibody Trk62 of the invention with a frozen section of human osteoclast tumor tissue.

The results of microscopic observation are shown in FIG. 5.

In the monoclonal antibody Trk62 group, cytoplasm alone of the osteoclasts was selectively stained in the frozen sections. In the paraffin sections, no response was observed at all. In the anti-TRAP antibody 9C5 group, no detectable response was observed in the frozen sections and in the paraffin sections, osteoclasts were stained.

These results proved that monoclonal antibody Trk62 can recognize TRACP 5b retaining the steric structure. This is also confirmed by the fact that the monoclonal antibody was reactive only with the frozen sections that retained the steric structure of enzyme. Moreover, the results proved that quick staining of samples provided for operation can be perioperatively made using the monoclonal antibody of the invention, which could assist to make histological diagnosis.

As described above in detail, the monoclonal antibody of the invention provides a higher reactivity with TRACP 5b than with TRACP 5a and a higher specificity to TRACP 5b. Therefore, TRACP 5b in a sample can be specifically detected by using the monoclonal antibody of the invention. The monoclonal antibody of the invention can specifically detect TRACP 5b as a marker for bone resorption with high sensitivity, and is thus extremely useful as an indicator of bone-associated disorders in clinical tests, etc.

We claim:

1. A hybridoma, which has been deposited at National Institute of Advanced Industrial Science and Technology, International Patent Organism Depositary, under the accession number of FERM BP-7890.

2. A monoclonal antibody to tartrate-resistant acid phosphate, which according to a measurement method, wherein the monoclonal antibody is reacted with TRACP 5a and TRACP 5b at pH 5.7, each having a same enzymatic activity of 10 U/L, non-bonded TRACP 5a and TRACP 5b are removed, each of bonded TRACP 5a and 5b are reacted with p-nitrophenyl-phosphate (pNPP) at pH 6.1 and an absorbance is measured at 405 nm, the absorbance value of TRACP 5b is greater by two or more times than that of TRACP 5a,
wherein the monoclonal antibody has been produced by a hybridoma deposited at National Institute of Advanced Industrial Science and Technology International Patent Organism Depositary, under the accession number of FERM BP-7890.

3. A monoclonal antibody to tartrate-resistant acid phosphatase 5b (TRACP 5b), which has a higher reactivity with and higher specificity to TRACP 5b by two or more times than that with or to tartarate-resistant acid phosphate 5a (TRACP 5a), as determined according to a measurement method, wherein the monoclonal antibody is reacted with TRACP 5b and TRACP 5a, respectively, each of which has a same enzymatic activity of 10 U/L as measured by a reaction of each with p-nitrophenylphosphate (pNPP) as a substrate at pH 5.7 in presence of tartaric acid or a tartrate, followed by a measurement of the absorbance at 405 nm; and then each of TRACP 5a and TRACP 5b having been reacted with and thus bounded to the monoclonal antibody is measured by a reaction of each of bounded TRACP 5b and TRACP 5a with pNPP at pH 6.1 in the presence of tartaric acid or a tartrate, followed by a measurement of the an absorbance at 405 nm,
wherein the monoclonal antibody has been produced by a hybridoma deposited at National Institute of Advanced Industrial Science and Technology, International Patent Organism Depositary, under the accession number of FERM BP-7890.

4. The monoclonal antibody according to claim 3, which does not show any substantial cross-reactivity with erythrocyte-, platelet-, neutrophil- and prostate-derived acid phosphatases.

5. The monoclonal antibody according to claim 1, which can recognize a steric structure of TRACP 5b retained in a native enzyme form.

6. A method for detection of TRACP 5b, comprising combining the monoclonal antibody of claim 1 with a sample in an immunoassay and determining a presence of TRACP 5b in said sample.

7. The method for detection according to claim 6, which further comprises detecting an enzyme activity of TRACP 5b having been combined with said monoclonal antibody of claim 1.

8. The method for detection according to claim 6, wherein said combining step further comprises
   a first step of dispensing said monoclonal antibody to a solid phase;
   a second step of adding said sample to said solid phase to bind said monoclonal antibody with TRACP 5b from said sample;
   a third step of adding a secondary antibody to said solid phase to react with TRACP 5b bound to said monoclonal antibody of to thereby form sandwich complexes; and
   a fourth step of measuring a concentration of said sandwich complexes to ascertain the concentration of TRACP 5b.

9. The method for detection according to claim 6, wherein said sample is human tissue.

10. A kit for use in detection of TRACP 5b comprising the monoclonal antibody of claim 1.

11. The kit according to claim 10, further comprising a solid phase support and an enzyme substrate of TRACP 5b.

12. The kit according to claim 10, further comprising a solid phase support, a labeled antibody specific for TRACP 5b other than said monoclonal antibody and a component for detecting the labeled antibody.

13. The kit according to claim 10, further comprising said monoclonal antibody as a first antibody, a labeled antibody as a second antibody and reagents for staining the labeled second antibody.

\* \* \* \* \*